(12) United States Patent
Marco Colas et al.

(10) Patent No.: US 10,150,736 B2
(45) Date of Patent: Dec. 11, 2018

(54) HAPTENS AND IMMUNOREACTIVE AGENTS AND USE THEREOF FOR PRODUCING FAMILY ANTIBODIES AND IMMUNOASSAYS FOR QUINOLONES

(75) Inventors: Maria Pilar Marco Colas, Barcelona (ES); Francisco José Sánchez Baeza, Barcelona (ES); Daniel González Pinacho, Barcelona (ES)

(73) Assignee: Consejo Superior de Investigaciones Cientificas (CSIC), Madrid (ES)

( * ) Notice: Subject to any disclaimer, the term of this patent is extended or adjusted under 35 U.S.C. 154(b) by 658 days.

(21) Appl. No.: 13/988,826

(22) PCT Filed: Nov. 21, 2011

(86) PCT No.: PCT/ES2011/070800
§ 371 (c)(1),
(2), (4) Date: Jun. 20, 2013

(87) PCT Pub. No.: WO2012/069683
PCT Pub. Date: May 31, 2012

(65) Prior Publication Data
US 2013/0273581 A1    Oct. 17, 2013

(30) Foreign Application Priority Data
Nov. 23, 2010 (ES) .................................. 201031721

(51) Int. Cl.
| | | |
|---|---|---|
| *G01N 33/94* | (2006.01) | |
| *C07D 401/10* | (2006.01) | |
| *C07K 16/44* | (2006.01) | |
| *C07D 215/56* | (2006.01) | |
| *C07D 215/233* | (2006.01) | |
| *C07D 401/12* | (2006.01) | |

(52) U.S. Cl.
CPC ....... *C07D 215/56* (2013.01); *C07D 215/233* (2013.01); *C07D 401/10* (2013.01); *C07D 401/12* (2013.01); *C07K 16/44* (2013.01); *G01N 33/9446* (2013.01)

(58) Field of Classification Search
None
See application file for complete search history.

(56) References Cited

U.S. PATENT DOCUMENTS

| | | |
|---|---|---|
| 4,868,305 A | 9/1989 | Cebula |
| 4,954,507 A | 9/1990 | Weber et al. |
| 5,032,518 A | 7/1991 | Huber et al. |
| 5,043,158 A | 8/1991 | Sleytr et al. |

FOREIGN PATENT DOCUMENTS

| | | |
|---|---|---|
| CN | 1827643 A | 9/2006 |
| CN | 1861632 A | 11/2006 |
| EP | 0 708 767 B1 | 2/2001 |
| ES | 2 043 900 T3 | 1/1994 |
| ES | 2 061 734 T3 | 12/1994 |
| ES | 2 156 128 T3 | 6/2001 |
| FR | 2437406 | 4/1980 |
| WO | WO 03/011297 A1 | 2/2003 |

OTHER PUBLICATIONS

The European Search Opinion issued for a European counterpart EP 2644596 A1, Application No. 2011843286, dated Feb. 18, 2014.*
Goodrow et al., "Strategies for Immunoassay Hapten Design," in Immunoanalysis of Agrochemicals; Nelson, J., et al.; ACS Symposium Series, 1995, vol. 586, Chapter 9, pp. 119-139.*
Wetzstein et al., "Degradation of Ciprofloxacin by Basidiomycetes and Identification of Metabolites Generated by the Brown Rot Fungus *Gloeophyllum striatum*," Appl. Environ. Microbiol., 1999, vol. 65, No. 4, pp. 1556-1563.*
Tittlemier et al., "Development of a direct competitive enzyme linked immunosorbent assay for the detection of fluoroquinolone residues in shrimp," Food Anal. Methods, 2008, vol. 1, issue 1, pp. 28-35.*
Ahmet Kamal et al.;Synthesis and Biological Activity of Fluoroquinolone-Pyrrolo[2,1-C][1,4]Benzodiazepine Conjugates; Bioorganic & Medicinal Chemistry 13 (2005) 2021-2029; accepted Jan. 7, 2005; available online at www.sciencedirect.com; 9 pages.
Anand V. Shindikar et al; Novel Fluoroquinolones: Design, Synthesis, and In Vivo Activity in Mice Against *Mycobacterium tuberculosis* $H_{37}Rv$; Bioorganic & Medicinal Chemistry Letters 15 (2005) 1803-1806; accepted Feb. 14, 2005; available online at www.sciencedirect,com; 4 pages.
Thomas Schwalbe et al.; Synthesis of a Library of Ciprofloxacin Analogues by Means of Sequential Organic Synthesis in Microreactors; QSAR Comb. Sci. 2005, 24; DOI: 10.1002/qsar.200540005; 2005 Wiley-VCH Verlag GmbH & Co. KGaA, Weinheim; pp. 758-768.
Fabien Giroud et al; Impedimetric Immunosensor Based on a Polypyrrole—Antibiotic Model Film for the Label-Free Picomolar Detection of Ciprofloxacin; Anal. Chem 2009, 81; 5 pgs; pp. 8405-8409.
Paul R. McGuirk et al.; Synthesis and Structure-Activity Relationships of 7-Diazabicycloalkylquinolones, Including Danofloxacin, a New Quinolone Antibacterial Agent for Veterinary Medicine; Journal of Medicinal Chemistry; vol. 35, No. 4; Feb. 21, 1992; XP002901194; 10 pgs.
Carol K. Holtzapple et al.; Production and Characterization of Monoclonal Antibodies against Sarafloxacin and Cross-Reactivity Studies of Related Fluoroquinolones; J. Agric. Food Chem. 1997, 45, 1984-1990; Published 1997 by the American Chemical Society; XP-002402239; 7 pgs.

(Continued)

*Primary Examiner* — Galina Yakovleva
(74) *Attorney, Agent, or Firm* — Reinhart Boerner Van Deuren P.C.

(57) ABSTRACT

The invention relates to haptens, immunogens and secondary immunoreactive agents, to the use thereof for producing wide-spectrum antibodies against quinolone-type antibiotics, to the application thereof to immunochemical analysis techniques, and to a kit enabling the detection of said antibiotics in biological samples from food products of animal origin.

4 Claims, No Drawings

(56) References Cited

OTHER PUBLICATIONS

Najim A. Al-Masoudi et al.; Synthesis of Acyclic 6,7-Dihaloquinolone Nucleoside Analogues as Potential Antibacterial and Antiviral Agents; Bioorganic & Medicinal Chemistry 8 (2000); 7 pgs.; pp. 1407-1413.
Marino Artico et al.; Nitroquinolones With Borad-Spectrum Antimycobacterial activity in Vitro; Bioorganic & Medicinal Chemistry Letters 9 (1999); 6 pgs. pp. 1651-1656.
Limin Cao et al; Broad-Specific Antibodies for a Generic Immunoassay of Quinolone: Development of a Molecular Model for Selection of Haptens Based on Molecular Field-Overlapping; Anal. Chem. 2009, 81; 6 pgs; pp. 2346-3251.
Tai-Li Tsou et al.; Synthesis and Antipseudomonal Activity of Fluoroquinolonyl-Penicillin Derivatives; Eur. J. Med. Chem. 34 (1999); 5 pgs.; pp. 255-259.
Watanabe, Hiroo et al.; Monoclonal-based Enzyme-linked Immunosorbent Assay and Immunochromatographic Assay for Enrofloxacin in Biological Matrices; The Analyst; 2002; 3 pages (98-103); vol. 127.
Holtzapple, Carol K. et al; Development of Antibodies Against the Fluoroquinolone Sarafloxacin and Molecular Modeling Studies of Cross-reactive Compounds; Food and Agricultural Immunology; 1997; 15 pages (cover sheet and 13-26) vol. 9.
Wang, Zhanhui et al.; Development of a Monoclonal Antibody-Based Broad-Specificity ELISA for Fluoroquinolone Antibiotics in Foods and Molecular Modeling Studies of Cross-Reactive Compounds; Analytical Chemistry; Jun. 15, 2007; 13 pages (4471-4483); vol. 79, No. 12.
Bucknall,S. et al; Antibodies to the Quinolones and Fluoroquinolones for the Development of Generic and Specific Immunoassays for Detection of These Residues in Animal Products; Food Additives and Contaminants; 2003; 9 pages (cover sheet and 221-228); vol. 20, No. 3.
Huet, Anne-Catherine et al.; Simultaneous Determination of (Fluoro)quinolone Antibiotics in Kidney, Marine Products, Eggs, and Muscle by Enzyme-Linked Immunosorbent Assay (ELISA); Journal of Agricultural and Food Chemistry; 2006; 6 pages (2822-2827); vol. 54.
Adrian, Javier et al.; Wavelength-interrogated Optical Biosensor for Multi-analyte Screening of Sulfonamide, Fluoroquinolone, β-lactam and Tetracycline Antibiotics in Milk; Trends in Analytical Chemistry; 2009; 9 pages (769-777); vol. 28, No. 6.
Kantiani, Lina et al.; Analytical Methodologies for the Detection of β-lactam Antibiotics in Milk and Feed Samples; Trends in Analytical Chemistry; 16 pages (729-744) vol. 28, No. 6.
Jiang, Yousheng et al.; Production and Characterization of Monoclonal Antibodies Against Small Hapten-ciprofloxacin; African Journal of Biotechnology; Oct. 24, 2011; 6 pages (14342-14347); vol. 10(65).
Hernández-Arteseros, J.A. et al.; Analysis of Quinolone Residues in Edible Animal Products; Journal of Chromatography A; 2002; 24 pages (1-24) vol. 945.
Council Directive 96/23/EC; On Measures to Monitor Certain Substances and Residues Thereof in Live Animals and Animal Products and Repealing Directives 85/358/EEC and 86/469/EEC and Decisions 89/187/EEC and 91/664/EEC; Official Journal of the European Communities; Apr. 29, 1996; 23 pages; No. L 125/10.
Council Regulation (EEC) No. 2377/90; Laying Down a Community Procedure for the Establishment of Maximum Residue Limits of Veterinary Medicinal Products in Foodstuffs of Animal Origin; Jun. 26, 1990; 110 pages (1-110).

\* cited by examiner

HAPTENS AND IMMUNOREACTIVE AGENTS AND USE THEREOF FOR PRODUCING FAMILY ANTIBODIES AND IMMUNOASSAYS FOR QUINOLONES

This invention relates to haptens, immunogens and secondary immunoreactive agents, their use for producing broad spectrum antibodies against quinolone antibiotics, and their application in immunochemical techniques for the analysis of said antibiotics in biological samples.

PRIOR ART

Food nutritional quality, availability and safety are essential to the welfare of society. The need for increasing animal productivity has resulted, in some particular situations, in the inappropriate use of drugs intended for veterinary use.

More specifically, quinolone antibiotics are not only used for therapeutic purposes, but also as a precautionary means in order to prevent diseases in farms with high stabling density. In this way, the development of bacterial resistance mechanisms are encouraged, drastically reducing the efficiency of treatment, when such bacteria are the source of human diseases.

Consequently, the European Agency for the Evaluation of Medicinal Products (EMEA) has established maximum residue limits (MRLs) in the different foodstuffs of animal origin in its Directive about food security 2377/90/CE. The Agency has also imposed a series of guidelines on inspection laboratories about the sampling frequency and the number of substances to be controlled before these products are available to consumers (Directive 96/23/CE). This creates the need for carrying out a high number of analyses.

Techniques that are currently used for quinolone detection are mainly Gas chromatography/mass spectrometry (GC-MS) and High-performance liquid chromatography (HPLC) with several types of detection (mostly ultraviolet and mass spectrometry) (Hernández-Arterseros, *J. Chromatography A*. 2002, 945, 1-24). The main drawback of these techniques is that they require complex instrumentation and skilled personnel, as well as previous preparation for the sample, which extends the time of analysis.

Microbiological assays are also used which, even though they are less expensive, the delay for obtaining results plus their own methodology make them unfeasible methods for rapid alarm. Therefore, current methods for sample analysis and preparation do not respond appropriately to the legislation requirements regarding the protection of public health. Immunochemical procedures provide important advantages such as screening procedures, due to their simplicity, costs and high processing capabilities.

Bibliography has already described several generic immunoassays for quinolones. In every case, the immunization hapten was a commercial quinolone bound to a immunogenic protein by means of carboxylic acid in the 3-position (Holtzapple, *Food and Agric. Immunol.* 1997, 9, 13-26; Bucknall, *Food Additives and Contaminants* 2003, 20, 221-228; Wang, *Anal. Chem.* 2007, 79, 4471-4483) or through remaining piperazine in the 7-position (Huet, *J. Agric. Food Chem.* 2006, 54, 2822-2827), thus blocking common and important epitopes from the quinolone family.

The prior art does not address the method for attaching the quinolone hapten to the immunogenic carrier through 1-position. In this way, haptens retain all epitopes characteristic of quinolones, maximizing their exposure to the immune system of the host animal while maintaining the acid-base properties intact of such compounds.

The present invention provides said haptens and immunoreactive agents derived thereof, which are useful for obtaining improved family antibodies against quinolones and provide better benefits when used in immunoassays for quinolone detection.

DESCRIPTION OF THE INVENTION

The present invention relates to a group of haptens that are structurally related, from a chemical perspective, with quinolone antibiotics. Likewise, the invention relates to immunoreactive agents derived from the binding of said haptens to immunogenic carriers and their use for obtaining antibodies with class selectivity for the quinolone family. The invention also makes reference to the use of any of these immunoreactive agents as secondary immunoreactive agents, and of any antibody produced thereof, in immunochemical methods for quinolone analysis in biological samples.

In accordance with one aspect of the invention, the present invention refers to a compound of formula (I):

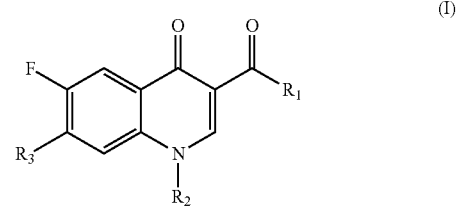

Or salts, isomers, or solvates thereof,
wherein:

$R_1$ is selected from OH, $C_1$-$C_{10}$ O-alkyl, $OR_4$, $NHR_4$, wherein $R_4$ is an immunogenic carrier;

$R_2$ is selected from H, $C_3$-$C_{10}$ alkyl, —$(CH_2)_m$—$R_5R_6$, where m is a value between 3 and 6 when $R_5$ is selected from O or NH, or m represents a value between 1 and 6 when $R_5$ is S and $R_6$ is selected from H, $C_1$-$C_6$ alkyl, aryl, alkyl-aryl, $R_4$ or $LR_4$, where L is a bifunctional linking compound;

$R_3$ is selected from heterocyclic compound, halogen or $NR_7R_8$, where $R_7$ and $R_8$ are selected independently from H, $C_1$-$C_6$ alkyl, —$(CH_2)_n$—$R_9R_{10}$, where n represents a value from 1 to 6, $R_9$ is selected from S, O or NH and $R_{10}$ is selected from H or $C_1$-$C_6$ alkyl, aryl, alkyl-aryl, $R_4$ or $LR_4$.

Preferably, $R_1$ is $C_1$-$C_6$ O-alkyl, and more preferably, O-ethyl.

Preferably, $R_1$ is OH.

Preferably, $R_1$ is $NHR_4$, where $R_4$ is a protein, and more preferably $R_4$ is selected from bovine serum albumin (BSA), concanavalin A (CONA), ovalbumin (OVA), horseradish peroxidase (HRP), keyhole limpet hemocyanin (KLH) or horseshoe crab hemocyanin (HCH).

Preferably, $R_2$ is —$(CH_2)_3$—$SR_6$ where $R_6$ is selected from H or $LR_4$, L is selected from maleimidopropanoato complexes and iodoacetyl, and $R_4$ is selected from BSA, CONA, HRP or HCH.

Preferably, $R_2$ is $C_3$-$C_6$ alkyl, and more preferably, $R_2$ is propyl.

Preferably, $R_3$ is selected from halogen or heterocycle. More preferably, $R_3$ is selected from fluorine or chlorine.

Preferably, R$_3$ is selected from the following group:

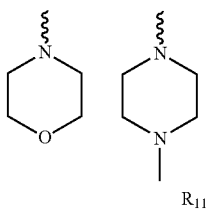

wherein R$_{11}$ is C$_1$-C$_6$ alkyl, preferably methyl.

Preferably, R$_3$ is NR$_7$R$_8$, wherein R$_7$ and R$_8$ are an alkyl group C$_1$-C$_6$, which may be the same or different. More preferably, R$_7$ and R$_8$ are ethyl.

Preferably, R$_3$ is NR$_7$R$_8$, wherein R$_7$ is H and R$_8$ is an alkyl group C$_1$-C$_6$, which may be substituted. More preferably, R$_3$ is —NH(CH$_2$)$_2$NH$_2$.

Preferably, the compound of formula (I) is selected from the following group:
- Ethyl 6,7-difluoro-4-oxo-1-propyl-1,4-dihydroquinoline-3-carboxylate.
- Ethyl 1-(3-(benzhydryl)propyl)-7-chlorine-6-fluoro-4-oxo-1,4-dihydroquinoline-3-carboxylate.
- Ethyl 1-(3-(benzhydryl)propyl)-6,7-difluoro-4-oxo-1,4-dihydroquinoline-3-carboxylate.
- 6,7-difluoro-4-oxo-1,4-dihydroquinoline-3-carboxylic acid.
- 6,7-difluoro-4-oxo-1-propyl-1,4-dihydroquinoline-3-carboxylic acid.
- 1-(3-(benzhydryl)propyl)-6,7-difluoro-4-oxo-1,4-dihydroquinoline-3-carboxylic acid.
- 6-fluoro-7-(N-morpholinyl)-4-oxo-1,4-dihydroquinoline-3-carboxylic acid.
- 6-fluoro-7-(N-morpholinyl)-4-oxo-1-propyl-1,4-dihydroquinoline-3-carboxylic acid.
- 7-(2-aminoethylamino)-6-fluoro-4-oxo-1-propyl-1,4-dihydroquinoline-3-carboxylic acid.
- 7-(diethylamino)-6-fluoro-4-oxo-1-propyl-1,4-dihydroquinoline-3-carboxylic acid.
- 1-(3-(benzhydryl)propyl)-6-fluoro-7-(N-morpholinyl)-4-oxo-1,4-dihydroquinoline-3-carboxylic acid.
- 1-(3-(benzhydryl)propyl)-6-fluoro-4-oxo-7-(N-piperazinyl)-1,4-dihydroquinoline-3-carboxylic acid.
- 6-fluoro-7-(4-methylpiperazin-1-yl)-4-oxo-1-propyl-1,4-dihydroquinoline-3-carboxylic acid.
- 6-fluoro-1-(3-mercaptopropyl)-7-(N-morpholinyl)-4-oxo-1,4-dihydroquinoline-3-carboxylic acid.
- 6-fluoro-1-(3-mercaptopropyl)-4-oxo-7-(N-piperazinyl)-1,4-dihydroquinoline-3-carboxylic acid.
- 1-[3-(2-acetamide BSA)tiopropyl]-6-fluoro-7-(N-morpholinyl)-4-oxo-1,4-dihydroquinoline-3-carboxylic acid.
- 1-[3-(2,5-dioxo-1-(3-(BSA carboxamide)propyl)pyrrolidin-3-ylthio)propyl]-6-fluoro-4-oxo-7-(N-piperazinyl)-1,4-dihydroquinoline-3-carboxylic acid.
- 1-[3-(2-acetamide HCH)thiopropyl]-6-fluoro-7-(N-piperazinyl)-4-oxo-1,4-dihydroquinoline-3-carboxylic acid.
- 1-[3-(2-acetamide BSA)thiopropyl]-6-fluoro-7-(N-piperazinyl)-4-oxo-1,4-dihydroquinoline-3-carboxylic acid.
- 6,7-difluoro-4-oxo-1,4-dihydroquinoline-3-carboxamide BSA.
- 6,7-difluoro-4-oxo-1,4-dihydroquinoline-3-carboxamide CONA.
- 6,7-difluoro-1-propyl-4-oxo-1,4-dihydroquinoline-3-carboxamide BSA.
- 6,7-difluoro-1-propyl-4-oxo-1,4-dihydroquinoline-3-carboxamide CONA.
- 6-fluoro-7-(N-morpholinyl)-4-oxo-1,4-dihydroquinoline-3-carboxamide BSA.
- 6-fluoro-7-(N-morpholinyl)-4-oxo-1-propyl-1,4-dihydroquinoline-3-carboxamide BSA.
- 7-[2-(BSA acetamide)ethylamino]-6-fluoro-4-oxo-1-propyl-1,4-dihydroquinoline-3-carboxylic acid.
- 7-(diethylamino)-6-fluoro-4-oxo-1-propyl-1,4-dihydroquinoline-3-carboxamide BSA.
- 7-(diethylamino)-6-fluoro-4-oxo-1-propyl-1,4-dihydroquinoline-3-carboxamide CONA.
- 6-fluoro-7-(4-methylpiperazin-1-yl)-4-oxo-1-propyl-1,4-dihydroquinoline-3-carboxamide BSA.
- 6-fluoro-7-(4-methylpiperazin-1-yl)-4-oxo-1-propyl-1,4-dihydroquinoline-3-carboxamide CONA.
- 7-[2-(4-chloro-6-HRP-1,3,5,-triazine-2-ylamino)ethylamino]-6-fluoro-4-oxo-1-propyl-1,4-dihydroquinoline-3-carboxylic acid.

Or salts, isomers or solvates thereof.

"Alkyl" is herein defined as straight or branched hydrocarbon chains of radicals having 1 to 10 carbon atoms, preferably 1 to 6, which are attached to the rest of the molecule by a single bond, for example, methyl, ethyl, n-propyl, i-propyl, n-butyl, tert-butyl, sec-butyl, n-pentyl, n-hexyl, and so on. Alkyl groups may be optionally substituted by one or more substituents, such as halogen (referred as haloalkyl), hydroxyl, alkoxy, aryl, carboxyl, carbonyl, cyano, acyl, alkoxycarbonyl, amino, nitro, mercapto and alkylthio.

The term "aryl", alone or in combination, refers herein to a system of mono- or polycyclic aromatic ring containing carbon ring atoms. Preferred aryl ring systems are 5-10 monocyclic or bicyclical members, such as phenyl or biphenyl, which optionally carry one or several substituents.

"Heterocycle" refers herein to a stable ring radical of 3-15 members consisting of carbon atoms and 1-5 heteroatoms selected from the group comprised by nitrogen, oxygen and sulphur, preferably a 4-8 membered ring with one or more heteroatoms, and more preferably, a 5 or 6-membered ring with one or more heteroatoms. For the purposes of this invention, the heterocycle may be a monocyclic, bicyclical or tricyclic ring, which may include condensed ring systems, and the nitrogen, carbon or sulphur atom in the heterocycle radical may be optionally oxidized, the nitrogen atom may be optionally quaternized, and the heterocyclic radical may be partially or fully saturated or be aromatic. Examples of said heterocycles include, but are not limited to azepines, benzimidazole, benzothiazole, furan, isothiazole, indole, piperidine, piperazine, azathioprine, quinoline, thiadiazole, tetrahydrofuran, coumarin, morpholine, pyrrole, pyrazole, oxazole, isoxazole, triazole, imidazole, among others.

"Halogen" refers to fluorine, chlorine, bromine or iodine.

"Immunogenic carrier" refers to those materials that have the property of independently generating an immune response in the host animal and that can be covalently bound to the haptens described in the present invention. A suitable carrier material includes, for instance, natural or synthetic polymeric compounds, such as polypeptides, and oligonucleotides, and proteins, such as albumin, serum proteins, globulins, lipoproteins and hemocyanins. Illustrative examples of immunogenic carrier include bovine serum protein, ovalbumin, concanavalin A, keyhole limpet hemocyanine and horseshoe crab hemocyanine.

Given that compounds of formula (I) have groups and atoms capable of losing or gaining charges, the present invention also refers to a compound of formula (I) in the form of a salt.

The compounds of the present invention represented by formula (I), and more specifically, the specific compounds belonging to this general formula described above may be comprised of isomers, depending on the presence of multiple bonds (for example, Z, E), including optical isomers or enantiomers, depending on the presence of chiral centers. Isomers, enantiomers or diastereomers and mixtures thereof fall within the scope of this invention. Enantiomers or diastereomers, and their mixtures, can be separated by conventional techniques.

In a second aspect, the present invention relates to the use of a compound of formula (I) as described above for producing broad spectrum antibodies against quinolone antibiotics.

Examples of quinolones are, but without limitation to, marbofloxacin, enrofloxacin, norfloxacin, ciprofloxacin, sarafloxacin, oxolinic acid, flumequine, ofloxacin, danofloxacin or difloxacin.

Another aspect of the invention refers to a method for producing antibodies against quinolone antibiotics, which comprises:
  a) Activation of an immunogenic carrier with a bifunctional linking compound;
  b) Conjugation of immunogenic carrier activated in (a) with a compound of formula (I);
  c) Immunization of a nonhuman animal with the conjugate obtained in (b);
  d) Extraction of antibodies generated in (c).

The immunogenic carrier may be any synthetic or natural polymer, oligonucleotide, polypeptide or protein for conjugation of haptens known in the art, but preferably selected from proteins such as bovine serum albumin, ovalbumin, concanavalin A, horseradish peroxidase, keyhole limpet hemocyanin or horseshoe crab hemocyanin.

Immunogenic carrier activation can be performed by any known biochemical technique, although in the process of this invention is preferably performed by reacting the immunogenic carrier with succinimidyl esters as the bifunctional linking compound.

"Bifunctional linking compound" refers to those compounds having two functional groups, usually at opposite ends of molecule, which are capable of reacting with other functional groups either incorporated to haptens or to immunogenic carriers. If the functional groups that should react with are identical, these compounds are homobifunctional linking compounds, and if the groups they should react with are different, these compounds are heterobifunctional linking compounds.

Another aspect of present invention relates to an antibody that is obtained by means of the procedure described.

Another aspect of the present invention relates to the use of said antibodies for the detection and/or quantification of quinolone antibiotics in an isolated biological sample. Preferably, this biological sample derives from a product of animal origin intended for food consumption, and more preferably, they are milk samples.

Another aspect of the present invention makes reference to the use of the compounds of formula (I) described above as secondary immunoreactive agents for the detection and/or quantification of quinolone antibiotics in an isolated biological sample. Preferably, this biological sample derives from a product of animal origin intended for food consumption, and more preferably, they are milk samples.

"Secondary immunoreactive agents" are defined as those reagents necessary in a competitive immunoassay for the detection of low molecular weight molecules. These may be coating antigens, which are used in competitive immunoassays of indirect format, and in which case they are attached to the solid support and compite with the analyte for the antibody in solution. Tracers can be enzymatic, fluorescent or radioactive, which are used in competitive immunoassays of direct format, and in which case they compite in solution with the analyte for the antigen immobilized upon the solid support.

Another aspect of the present invention relates to a kit for the detection and/or quantification of quinolone antibiotics comprising at least one antibody or compound of formula (I), as described above. The kit components may be attached to different types of carriers known in the prior art, such as nitrocellulose, for polystyrene plates or strip test for ELISA assays. Also, the kit may include other components and reagents necessary to carry out sample analysis.

Another aspect of the present invention refers to the use of above described detection kit for determining and/or quantifying quinolone antibiotics in foodstuffs of animal origin. Illustrative examples of foodstuffs of animal origin include milk and milk products, eggs, meat (muscle, kidney, liver, etc.) from different animal species.

The use of the term "comprise" and its variants throughout description and claims sections do not intend to exclude other technical features, additives, components or steps. For those skilled in the art, other objects, advantages and features of the invention will become apparent from the specification and practice of the invention. The following examples and drawings are provided by way of illustration, and are not intended to be limiting of the present invention.

EXAMPLES

Hapten Synthesis

Compounds of formula (I) may be prepared according to various methods known to anyone skilled in the field of organic synthesis, particularly, general procedures that are shown in the following schemes. Starting materials for preparative methods are commercially available or can be prepared using the methods described in the literature.

Compounds of formula (I) can be obtained from the methods and schemes described below:

According to Goulds-Jacobs method (see scheme 1), corresponding aniline is made react with diethyl ethoxymethylenemalonate in an addition-elimination reaction to obtain malonate II. Then, it is made react in diphenyl ether at high temperature to give place to 4-oxoquinoline III. After that, the quinolone nitrogen is alkylated with a halide in a basic medium to obtain 1-alkyl(substituted)-4-oxoquinoline Ia. The ester is hydrolyzed in basic medium to obtain the corresponding carboxylic acid Ib, which is made react with an amine in aromatic nucleophilic substitution to obtain 7-amino-4-oxoquinoline Ic.

In case that the amine used to form compound Ic is piperazine, the sequence is continued methylating the piperazine nitrogen using formaldehyde and formic acid or any methylating agent as methyl iodide or dimethyl sulfate.

Scheme 1

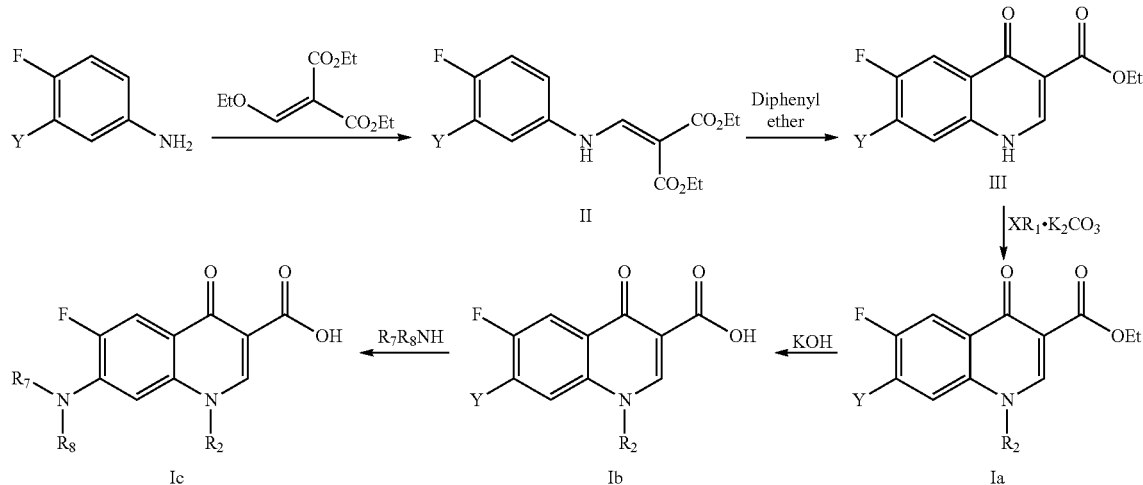

An alternative strategy for obtaining compounds of formula I may be Grohe-Heitzer's (see scheme 2). In this strategy, the chloride corresponding to the benzyl acid is acylated to obtain the malonic ester, which is in turn condensed under dehydrating conditions using an orthoester to give the enol ether. Said ether undergoes an addition-elimination reaction with corresponding primary amine, and the resulting product is cyclized in a tandem addition-elimination reaction in the ortho position.

field of organic and immunochemical synthesis, particularly, general procedures that are shown in the following schemes. Starting materials for preparative methods are commercially available or can be prepared using the methods described in the literature.

a). Haptens with a Thiol Group

Haptens with a thiol group are covalently attached to immunogenic carriers (SI), which are activated with groups Scheme 2

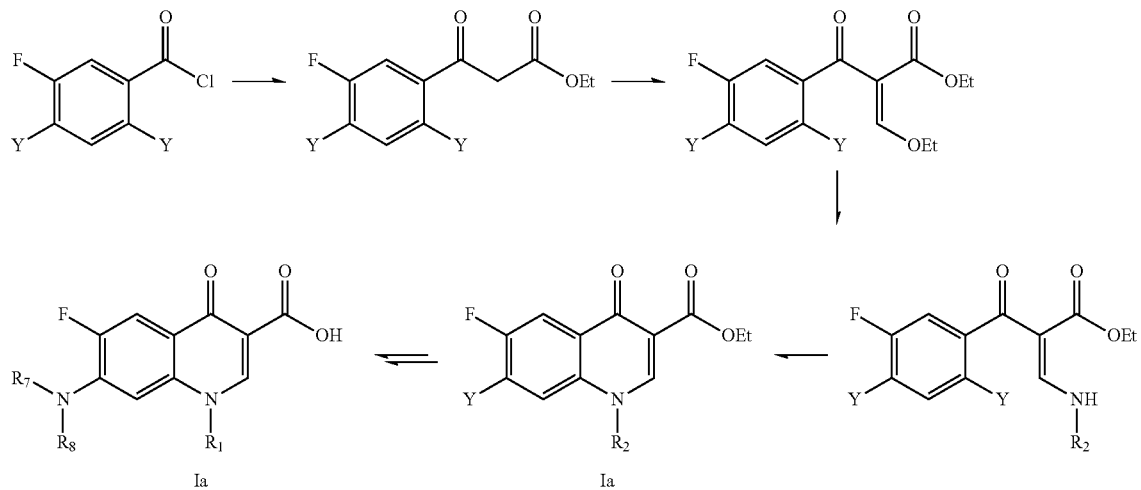

Amines and alkyl halide used are commercially available or can be obtained through known methods (March, *Advanced Organic Chemistry*. 1991, Ed. John Wiley & Sons).

Thiols used are commercially available and their protection and deprotection can be performed by known methods (Green, *Protective Groups in Organic Chemistry*. 1999, Ed. John Wiley & Sons).

Preparation of Immunoreactive Agents

Immunoreactive agents of formula (I) may be prepared according to various methods known to anyone skilled in the capable of reacting with said thiol group (see scheme 3) by means of heterobifunctional linking compounds.

1. Immunogenic carrier activation. Immunogenic carriers are made react with succinimidyl esters o with any other active ester or activator of carboxylic acids reactivity, having in their structure reactive features with the thiol group.
2. Thiol group deprotection. In parallel, we proceed to thiol group deprotection following appropriate methodology for the corresponding protective group.
3. Immunoconjugate. Unprotected hapten is made react with activated immunogenic carrier.

Scheme 3
1. 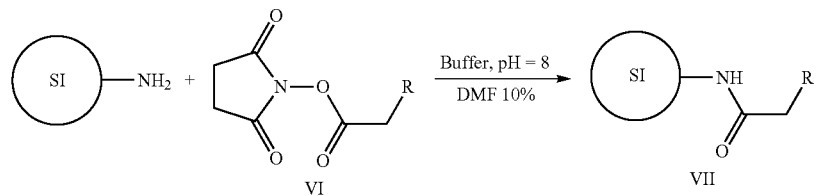
2. 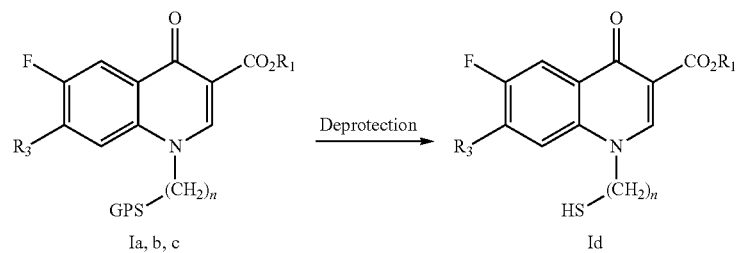
3. 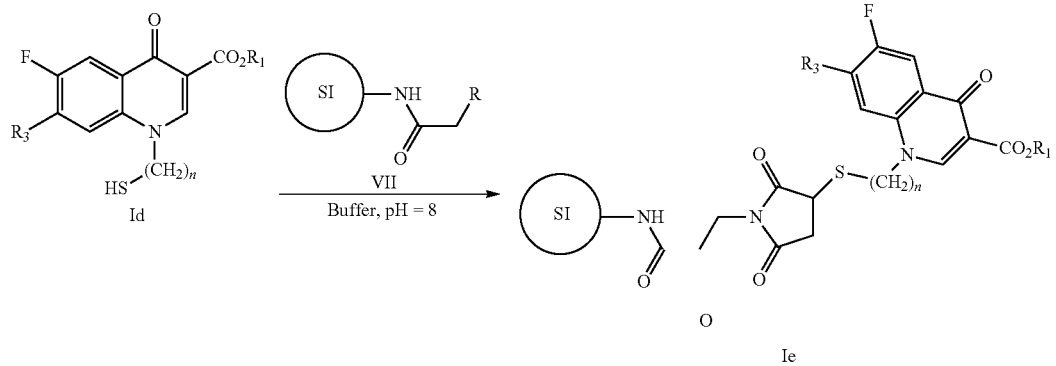
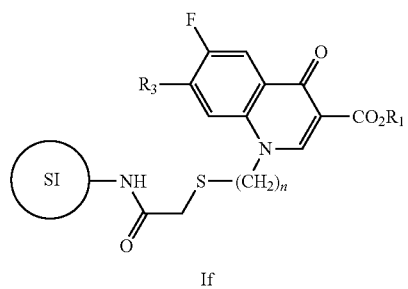

Activating agents for carboxylic acids are commercially available, just like succinimidyl esters, or can be obtained by known methods (March, *Advanced Organic Chemistry*. 1991, Ed. John Wiley & Sons) or using the schemes described below as an example.

Succinimidyl esters can be obtained through reaction of corresponding acid with N-hydroxysuccinimide using any carbodiimide as activator, for example, dicyclohexycarbodiimide (see scheme 4, Hampton, *J. Med. Chem.* 1976, 19, 1279-1283).

Scheme 4

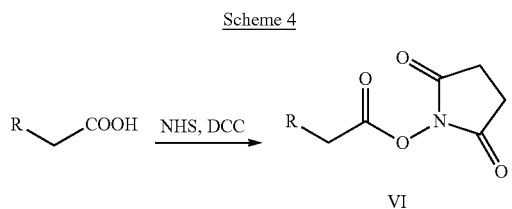

b) Haptens with NH or COOH Group

In the case of haptens with amine and carboxylic groups, they are conjugated with the immunogenic carriers using carbodiimide reaction or any other activator of carboxylic acids reactivity, either derived from the hapten or immunogenic carrier (see scheme 5).

Scheme 5

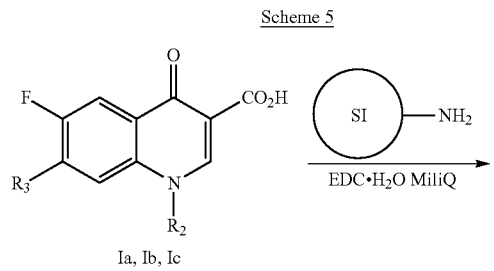

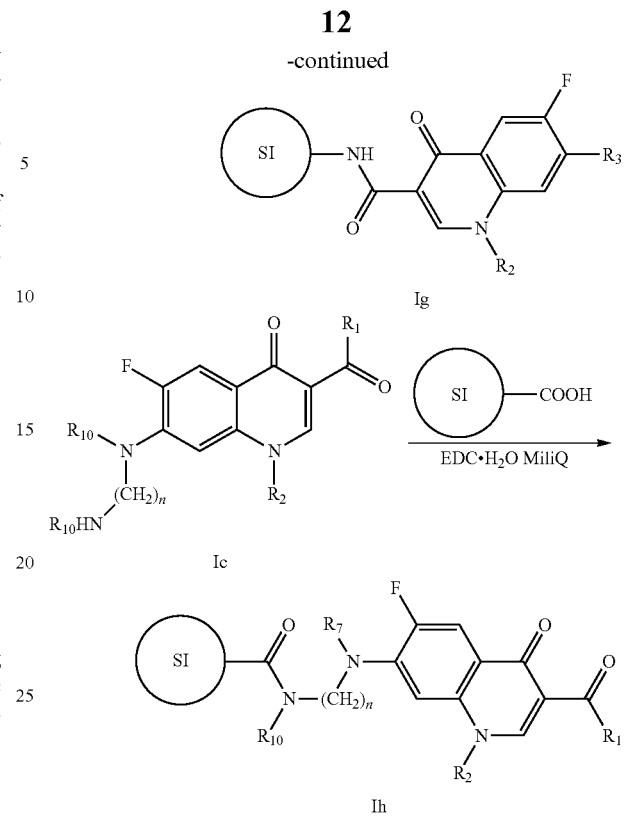

c) Haptens with $NH_2$ Groups

In the case of haptens with amine groups, they are also conjugated with immunogenic carriers that are previously functionalized through their amine groups, using homobifunctional linking compound. Such homobifunctional binding compounds may be cyanuric chloride, bis-imidoesters, bis-N-succinimidyl, diisocyanates or diisothiocyanates, biacilizides, dihaldehydes, diketones or any compound capable of reacting with several amine groups in different steps (see scheme 6).

Scheme 6

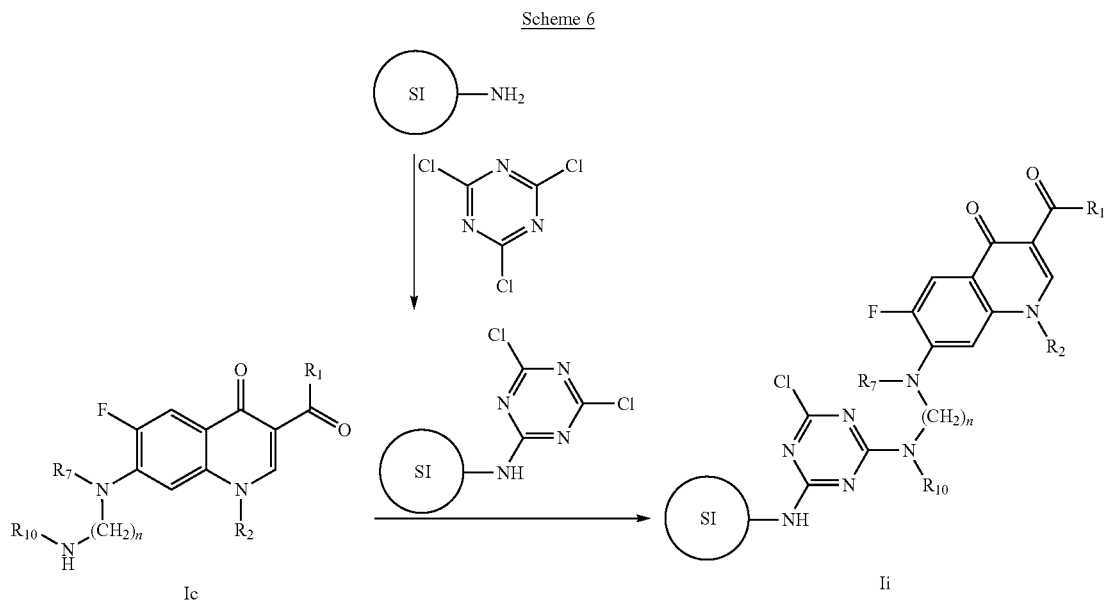

We will proceed to illustrate the invention using some tests performed by the inventors, which show the specificity and effectiveness of compounds of formula (I) as haptens and immunoreactive agents for the production of anti-fluoroquinolone antibodies and development of immunoassays for detecting said antibiotics.

A. Chemistry

General Procedures and Equipment

Thin layer chromatography was performed on aluminum sheets precoated with silica gel 60 F254 (Merck, Gibbstown, N.J.), and separation from the different compounds synthesized, when necessary, were carried out by means of column chromatography using silica gel 60 A C.C. (37-70 μm SDS). $^1$H y RMN $^{13}$C NMR spectra were obtained using Mercury-400 Varian spectrometer (Varian Inc., Palo Alto, Calif.) (400 MHz for $^1$H and 100 MHz for $^{13}$C). Chemical reagents used in this synthesis were obtained from ACROS ORGANICS (Geel, Belgium).

Preparation of Intermediates

Intermediate II

A mixture of corresponding 3,4-dihaloaniline (10 mmol) was heated together with diethyl ethoxymethylenemalonate (10 mmol) at 120° C. with stirring. A gentle stream of nitrogen was run during the 2 hours of the reaction in order to remove the ethanol formed. Subsequently, the mixture was dried under reduced pressure to obtain desired product.

Using this methodology, and corresponding aniline, the following malonates were prepared:

dietil 2-[(3-chloro-4-fluorophenylamino)methylene]malonate (IIa, 90% yield). 1H NMR (CDCl$_3$) δ ppm: 1.32 (3 H, t, J=7.14 Hz), 1.36 (3 H, t, J=7.14 Hz), 4.24 (2 H, q, J=7.14 Hz), 4.29 (2 H, q, J=7.14 Hz), 6.98 (1 H, ddd, J=8.97, 3.84, 2.93 Hz), 7.14 (1 H, t, J=8.60 Hz), 7.18 (1 H, dd, J=6.04, 2.93 Hz), 8.36 (1 H, d, J=13.36 Hz), 10.97 (1 H, d, J=13.36 Hz). 13C NMR (CDCl$_3$) δ ppm: 14.23 (1 C, s) 14.39 (1 C, s) 60.29 (1 C, s) 60.59 (1 C, s) 94.57 (1 C, s) 116.83 (1 C, d, J=6.84 Hz), 117.60 (1 C, d, J=22.23 Hz), 119.19 (1 C, s) 122.33 (1 C, d, J=18.81 Hz), 136.18 (1 C, d, J=2.99 Hz), 151.69 (1 C, s) 155.28 (1 C, d, J=247.05 Hz), 165.42 (1 C, s), 168.91 (1 C, s).

dietil 2-[(3,4-chloro-4-difluorophenylamino)methylene]malonate (IIb, 90% yield). 1H NMR (CDCl$_3$) δ ppm: 1.30 (3 H, t, J=7.14 Hz), 1.35 (3 H, t, J=7.14 Hz), 4.22 (2 H, q, J=7.14 Hz), 4.28 (2 H, q, J=7.07 Hz), 6.78-6.87 (1 H, m), 6.96 (1 H, ddd, J=11.16, 6.59, 2.74 Hz), 7.15 (1 H, q, J=8.78 Hz), 8.34 (1 H, d, J=13.54 Hz), 10.96 (1 H, d, J=13.36 Hz). 13C NMR (CDCl$_3$) δ ppm: 14.20 (1 C, s) 14.35 (1 C, s) 60.25 (1 C, s) 60.56 (1 C, s) 94.51 (1C, s) 106.56 (1C, d, J=20.94 Hz), 113.01 (1C, dd, J=6.20, 3.63 Hz), 118.33 (1 C, dd, J=18.81, 1.28 Hz), 136.04 (1C, dd, J=7.69, 2.99 Hz), 147.47 (1 C, dd, J=246.62, 12.82 Hz), 150.82 (1 C, dd, J=250.04, 13.68 Hz), 151.63 (1 C, s) 165.34 (1 C, s) 168.88 (1 C, s).

Intermediate III

Corresponding malonate II (9 mmol) was dissolved in diphenyl ether (15 mL), and resulting solution was heated to reflux. After 2 hours, the mixture was cooled at room temperature and hexane was added. The resulting solid was filtered, washed and dried to obtain desired product.

Using this methodology, and corresponding malonate, the following 4-oxo-1,4-dihydroquinoline-3-carboxylates were prepared:

Ethyl 7-chloro-6-fluoro-4-oxo-1,4-dihydroquinolone-3-carboxylate (IIIa, 92% yield). $^1$H NMR (CDCl$_3$) δ ppm: 1.32 (3 H, t, J=7.14 Hz), 4.47 (2 H, q, J=7.26 Hz), 8.10 (1 H, d, J=2.38 Hz), 8.12 (1 H, s) 9.11 (1 H, s); $^{13}$C NMR (CDCl$_3$) δ ppm: 13.60 (1 C, s) 67.53 (1 C, s) 107.03 (1 C, s) 111.70 (1 C, s) 121.68 (1 C, d, J=8.98 Hz), 124.42 (1 C, s) 137.21 (1 C, d, J=21.37 Hz), 138.00 (1 C, d, J=1.28 Hz), 147.31 (1 C, d, J=1.71 Hz), 160.23 (1 C, d, J=260.30 Hz), 169.04 (1 C, s) 174.53 (1 C, d, J=4.27 Hz).

Ethyl 6,7-difluoro-4-oxo-1,4-dihydroquinoline-3-carboxylate (IIIb, 85% yield). $^1$H NMR (CDCl$_3$) δ ppm: 1.33 (3 H, t, J=7.14 Hz), 4.49 (2 H, q, J=7.07 Hz), 7.83 (1 H, d, J=8.87, 6.31 Hz), 8.20 (1 H, t, J=8.33 Hz), 9.14 (1 H, s); $^{13}$C NMR (CDCl$_3$) δ ppm: 13.84 (1 C, s) 66.67 (1 C, s) 106.94 (1 C, s) 110.34 (1 C, d, J=22.23 Hz), 113.75 (1 C, dd, J=20.94, 2.99 Hz), 119.30 (1 C, dd, J=8.12, 1.28 Hz), 139.17 (1 C, d, J=11.54 Hz), 147.42 (1C, d, J=0.86 Hz), 153.97 (1C, dd, J=262.65, 14.75 Hz), 159.35 (1 C, dd, J=270.13, 15.81 Hz), 169.01 (2 C, s) 174.35 (1 C, d, J=4.27 Hz).

Intermediate IV

A mixture of chloroalkylthio (15 mmol) and diphenylmethanol (15 mmol) was dissolved in trifluoroacetic acid (30 mL) in a round bottom flask equipped with magnetic stirring at room temperature. Reaction was finished alter 2 hours as observed by thin layer chromatography (dichloromethaneas eluent). Mixture was dried under reduced pressure. Residue was dissolved in diethyl ether and washed with water and brine. Organic extracts were dried with anhydrous magnesium sulfate, and evaporated to dryness to obtain desired product.

Using this methodology, and corresponding chloroalkylthio, the following compounds were prepared:

Benzhydryl(3-chloropropyl)sulphane (IVa, 90% yield). $^1$H NMR (CDCl$_3$) δ ppm: 1.85 (2 H, dt, J=13.36, 6.68 Hz), 2.43 (2 H, t, J=7.04 Hz), 3.47 (2H, t, J=6.40 Hz), 4.81-5.28 (1 H, m), 7.07-7.15 (2 H, m), 7.17-7.24 (4 H, m), 7.29-7.36 (4 H, m); NMR $^{13}$C (CDCl$_3$) δ ppm: 29.19 (1 C, s), 31.64 (1 C, s), 43.42 (1 C, s), 54.13 (1 C, s), 127.18 (1 C, s), 128.17 (1 C, s), 128.51 (1 C, s), 141.10 (1 C, s).

Intermediate V

A mixture of sodium iodide (25 mmol) and IV (13 mmol) was dissolved in acetone (25 mL) and refluxed under inert atmosphere with stirring. After 7 hours, complete conversion of chlorine atom was observed by $^1$H MNR. Mixture was dried at reduced pressure and resulting residue was dissolved in methyl tert-butyl ether and washed with water and saturated sodium bisulphite in water. Organic extracts were dried with anhydrous magnesium sulfate, filtered and evaporated to dryness to obtain desired product.

Using this methodology, and corresponding protected chloroalkylthio, the following compounds were prepared:

Benzhydryl (3-iodopropyl) sulphane (Va, 80% yield). $^1$H NMR (CDCl$_3$) δ ppm: 1.89 (2 H, dt, J=13.67, 6.84 Hz), 2.38 (2 H, t, J=6.96 Hz), 3.12 (2 H, t, J=6.84 Hz), 5.04 (1 H, s), 7.13 (2 H, s, J=7.48, 7.48, 1.83, 1.53 Hz), 7.21 (4 H, t, J=7.57 Hz), 7.30 7.33 (4 H, m); NMR $^{13}$C (CDCl$_3$) δ ppm: 5.04 (1 C, s), 32.42 (1 C, s), 32.74 (1 C, s), 54.16 (1 C, s), 127.26 (1 C, s), 128.24 (1 C, s), 128.59 (1 C, s), 141.13 (1 C, s).

Intermediate VI

On a solution of N-hydroxysuccinimide (12.6 mmol) and dicyclohexylcarbodiimide (20.3 mmol) at 0° C., corresponding acid (6 mmol) was added and allowed to react for 4 hours at room temperature. In the case of compound VIa, a solution of maleic anhydride (10 mmol) and β-alanine was added in N,N-dimethylformamide, which has been previously made react for 1 hour. After 4 hours, mixture was evaporated at reduced pressure and the crude was dissolved in dichloromethane and washed with water. Organic extracts were dried with anhydrous magnesium sulfate, filtered and evaporated to dryness. Resulting residue was recrystallized to give desired compound.

Using this methodology, and corresponding acid, the following compounds were prepared:

3-succinimidyl maleimidopropionate (VIa, 25% yield). $^1$H NMR (CDCl$_3$) δ ppm: 2.82 (4 H, s), 3.02 (2 H, t, J=7.07 Hz), 3.94 (2 H, t, J=7.07 Hz), 6.74 (2 H, s); $^{13}$C NMR (CDCl$_3$) δ ppm: 25.5 (2 C, s), 29.7 (1 C, s), 32.9 (1 C, s), 134.3 (2 C, s), 166.0 (1 C, s), 168.7 (2 C, s), 170.1 (2 C, s).

Succinimidyl iodoacetate (VIb, 30% yield). $^1$H NMR (CDCl$_3$) δ ppm: 2.87 (2 H, s), 3.96 (1 H, s); 13C NMR (CDCl$_3$) δ ppm: −12.47 (1 C, s) 25.85 (2 C, s) 164.78 (1 C, s) 168.78 (2 C, s).

Preparation of Haptens

Hapten Ia

Anhydrous potassium carbonate (5 mmol) was added to a solution of corresponding 4-oxo-dihydroquinoline-3-carboxylate III (2 mmol) and alkyl halides (substituted V) (10 mmol) in anhydrous DMF (5 mL) and stirred for 10 hours at 110° C. in inert atmosphere. Mixture was evaporated under vacuum and resulting residue was dissolved in dichloromethane and washed with water and saturated sodium bisulphite in water. Organic phase was dried with MgSO4 and evaporated to dryness. When necessary, the crude was purified by means of liquid chromatography on silica gel using dichloromethane:ethyl acetate (9:1) as mobile phase to obtain desired product.

Using this methodology, and corresponding 4-oxo-1,4-dihydroquinoline-3-carboxylate, the following 1-alkyl-4-oxo-1,4-dihydroaquinoline-3-carboxylates were prepared:

Ethyl 6,7-difluoro-4-oxo-1-propyl-1,4-dihydroquinoline-3-carboxylate (I1, 80% yield). $^1$H NMR (TFAd) δ ppm: 0.97 (3 H, t, J=7.32 Hz), 1.36 (3 H, t, J=7.14 Hz), 1.98 (2 H, td, J=15.09, 7.50 Hz), 4.52 (2 H, q, J=7.14 Hz), 4.61 (2 t, J=7.69 Hz), 7.91 (1 H, dd, J=10.43, 6.22 Hz), 8.33 (1 H, t, J=8.42 Hz), 9.18 (1 H, s); RMN $^{13}$C (TFAd) δ ppm: 10.56 (1 C, s) 13.93 (1 C, s) 24.00 (1 C, s) 61.39 (1 C, s) 66.81 (1 C, s) 107.02 (1 C, s) 109.01 (1 C, d, J=24.36 Hz), 115.07 (1 C, dd, J=20.52, 3.42 Hz), 120.64 (1 C, d, J=8.12 Hz), 139.67 (1 C, d, J=10.69 Hz), 150.83 (1 C, s) 153.64 (1 C, dd, J=263.29, 14.53 Hz), 159.37 (1 C, dd, J=269.70, 15.39 Hz), 168.67 (1 C, s) 173.38 (1 C, d, J=3.85 Hz).

Ethyl 1-(3-(benzhydrylthio)propyl)-7-chlorine-6-fluoro-4-oxo-1,4-dihydroquinoline-3-carboxylate (I2, 80% yield). 1H NMR (DMSO-D6) δ ppm: 1.27 (3 H, t, J=7.14 Hz), 1.91 (2 H, quin, J=7.32 Hz), 2.37 (2 H, t, J=7.23 Hz), 4.22 (2 H, q, J=7.14 Hz), 4.36 (2 H, t, J=6.86 Hz), 5.31 (1 H, s) 7.17 (2H, t, J=7.32 Hz), 7.25 (4 H, t, J=7.41 Hz), 7.38 (4 H, d, J=7.32 Hz), 8.00 (1H, d, J=9.51 Hz), 8.07 (1 H, d, J=6.04 Hz), 8.60 (1H, s); 13C NMR (DMSO-D6) δ ppm: 13.68 (1 C, s) 27.24 (1 C, s) 27.58 (1C, s) 51.33 (1 C, s) 51.94 (1 C, s) 59.31 (1 C, s) 109.05 (1 C, s) 111.89 (1 C, d, J=22.23 Hz), 119.40 (1 C, s) 124.86 (1 C, d, J=19.66 Hz), 126.42 (2 C, s) 127.25 (4C, s) 127.82 (4C, s), 128.03 (1C, d, J=5.56 Hz), 135.13 (1 C, d, J=1.28 Hz), 140.85 (2 C, s) 149.29 (1 C, s) 153.74 (1 C, d, J=247.48 Hz), 163.60 (1C, s) 170.71 (1C, d, J=2.14 Hz).

Ethyl 1-(3-(benzhydrylthio)propyl)-6-7-difluoro-4-oxo-1,4-dihydroquinoline-3-carboxylate (I3, 75% yield). 1H NMR (TFAd) δ ppm: 1.36 (3H, t, J=7.23 Hz), 2.09 (2 H, quin, J=7.14 Hz), 2.48 (2 H, t, J=6.50 Hz), 4.52 (2 H, q, J=7.14 Hz), 4.69 (2 H, t, J=7.04 Hz), 4.97 (1H, s) 7.04-7.09 (2 H, m) 7.12 (4 H, t, J=7.23 Hz), 7.20 (4 H, d, J=7.14 Hz), 7.90 (1H, dd, J=10.15, 6.13 Hz), 8.31 (1 H, t, J=8.45 Hz), 9.22 (1 H, s); 13C NMR (TFAd) δ ppm: 13.93 (1 C, s) 28.58 (1C, s) 29.83 (1C, s) 56.63 (1C, s) 58.38 (1C, s) 66.76 (1 C, s) 106.86 (1C, s) 109.00 (1 C, d, J=23.51 Hz), 115.07 (1 C, dd, J=20.52, 2.99 Hz), 120.48 (1C, d, J=6.84 Hz), 128.26 (2 C, s) 129.27 (4 C, s) 130.10 (4 C, s) 139.44 (1 C, d, J=9.83 Hz), 141.79 (2 C, s) 151.39 (1C, s) 153.55 (1 C, dd, J=263.29, 14.53 Hz), 159.26 (1C, dd, J=269.70, 15.39 Hz), 168.54 {1C, s) 173.39 (1C, d, J=4.28 Hz).

Hapten Ib

A solution of 4-oxo-1,4-dihydroquinoline-3-carboxylate or the corresponding III or Ia (1 mmol) and potassium hydroxide (2.5 mmol) was refluxed in a mixture of THF:water (3:1, 4 mL) with stirring for 4.5 hours. Reaction crude was poured on a mixture of ice-water (50 mL), acidified with 1 M HCM; resulting precipitate was filtered and washed with cold water to obtain corresponding carboxylic acids.

Using this methodology, and corresponding carboxylate, the following carboxylic acids were prepared:

6,7-clifluoro-4-oxo-1,4-dihydroquinoline-3-carboxylic acid (I4, 80% yield). $^1$H NMR (TFAd) δ ppm: 7.86 (1 H, dd, J=8.87, 6.31 Hz), 8.24 (1 H, t, J=8.33 Hz), 9.23 (1 H, s); NMR $^{13}$C (TFAd) δ ppm 106.10 (1 C, s) 110.46 (1 C, dd, J=22.44, 1.07 Hz), 113.91 (1 C, dd, J=20.52, 2.99 Hz), 119.29 (1 C, dd, J=7.91, 1.50 Hz), 139.38 (1 C, d, J=11.54 Hz), 148.16 (1 C, d, J=1.71 Hz), 154.06 (1 C, dd, J=263.29, 14.53 Hz), 159.55 (1 C, dd, J=270.99, 15.81 Hz), 171.52 (1 C, s) 174.56 (1 C, d, J=4.27 Hz).

6,7-difluoro-4-oxo-1-propyl-1,4-dihydroquinoline-3-carboxylic acid (I5, 95% yield), $^1$H NMR (TFAd) δ ppm: 0.94 (4 H, t, J=7.41 Hz), 1.96 (2 H, td, J=15.00, 7.50 Hz), 4.60 (2 H, t, J=7.69 Hz), 7.90 (1 H, dd, J=10.34, 6.13 Hz), 8.31 (1 H, t, J=8.42 Hz); $^{13}$C NMR (TFAd) δ ppm: 10.59 (1 C, s) 24.00 (1 C, s) 61.52 (1 C, s) 106.32 (1 C, s) 109.16 (1C, d, J=23.51 Hz), 115.27 (1 C, dd, J=20.52, 2.99 Hz), 120.69 (1 C, d, J=7.27 Hz), 139.95 (1 C, d, J=9.83 Hz), 151.65 (1 C, s) 153.74 (1 C, dd, J=263.93, 14.32 Hz), 159.56 (1 C, dd, J=270.13, 15.39 Hz), 171.09 (1 C, s) 173.67 (1 C, d, J=3.85 Hz).

1-(3-(benzhydrylthio)propyl)-6,7-difluoro-4-oxo-1,4-dihydroquinoline-3-carboxylic acid (I6, 85% yield), $^1$H NMR (DMSO-D6) δ ppm: 1.96 (2 H, dt, J=14.41, 7.16 Hz), 2.36 (2 H, t, J=7.44 Hz), 4.49 (2 H, t, J=6.86 Hz), 5.29 (1 H, s) 7.17 (1 H, t, J=7.23 Hz), 7.24 (4 H, t, J=7.41 Hz), 7.36 (4 H, d, J=7.14 Hz), 8.15 (1 H, dd, J=12.26, 6.59 Hz), 8.23 (1 H, dd, J=10.34, 8.87 Hz), 8.90 (1 H, s); NMR $^{13}$C (101 MHz, DMSO-D6) δ ppm: 27.33 (1 C, s) 27.45 (1 C, s) 51.76 (1 C, s) 52.25 (1 C, s) 106.99 (1 C, d, J=22.65 Hz), 108.54 (48 C, s) 112.79 (1 C, d, J=18.38 Hz), 122.75 (1 C, d, J=4.27 Hz), 126.39 (2 C, s) 127.25 (4 C, s) 127.82 (4 C, s) 136.13 (1 C, d, J=10.26 Hz), 140.78 (1 C, s) 147.41 (1C, dd, J=249.83, 14.32 Hz), 148.99-149.42 (1 C, m) 152.65 (1 C, dd, J=253.89, 14.96 Hz), 164.98 (1C, s) 175.47 (1C, d, J=1.71 Hz).

Hapten Ic1

A solution of 4-oxo-1,4-dihydroquinoline Ia or Ib (0.75 mmol) and corresponding amine (1.9 mmol) was heated in anhydrous DMSO (2 mL) at 110° C. in inert atmosphere. After 5 hours, the solvent was removed at high vacuum, and the residue was dissolved in dichloromethane and washed with water and brine. Finally, the organic phase was dried with MgSO4 and evaporated to dryness.

Using this methodology, and corresponding 4-oxo-1,4-dihydroquinoline, the following 7-amine-4-oxo-1,4-dihydroquinolines were prepared:

6-fluoro-7-(N-morpholinyl)-4-oxo-1,4-dihydroquinoline-3-carboxylic acid (I7, 60% yield). $^1$H NMR (TFAd) δ ppm: 3.54-3.63 (4 H, m) 4.03-4.11 (4 H, m) 7.36 (1 H, d, J=6.95 Hz), 8.04 (1 H, d, J=12.81 Hz), 9.08 (1 H, s); NMR $^{13}$C (TFAd) δ ppm 50.96 (2 C, d, J=6.41 Hz), 67.74 (2 C, s) 104.42 (1 C, 30 s) 107.21 (1 C, d, J=4.27 Hz), 112.24 (1 C, d, J=26.07 Hz), 115.74 (1 C, d, J=10.26 Hz), 139.34-141.64

(1 C, m) 146.83 (1 C, s) 150.38 (1 C, d, J=10.69 Hz), 157.04 (1 C, d, J=259.02 Hz), 172.37 (1 C, s) 172.66 (1 C, d, J=4.70 Hz).

6-fluoro-7-(N-morpholinyl)-4-oxo-1-propyl-1,4-dihydroquinoline-3-carboxylic acid (I8, 70% yield). $^1$H NMR (TFAd) δ ppm: 0.94 (3 H, t, J=7.41 Hz), 1.97 (2 H, td, J=14.68, 7.23 Hz), 3.54-3.59 (4 H, m) 4.01-4.07 (4 H, m) 4.56 (2 H, t, J=7.32 Hz), 7.19 (1 H, d, J=6.77 Hz), 8.07 (1 H, d, J=12.81 Hz), 9.04 (1 5 H, s); NMR $^{13}$C (TFAd) δ ppm 10.74 (1 C, s) 23.47 (1 C, s) 51.03 (2 C, d, J=6.41 Hz), 60.72 (2 C, s) 67.90 (1 C, s) 104.56 (1 C, s) 105.60 (1 C, d, J=3.85 Hz), 113.43 (1 C, d, J=25.64 Hz), 116.94 (1 C, d, J=9.83 Hz), 141.08 (1 C, s) 150.32 (1 C, s) 150.60 (1 C, d, J=10.26 Hz), 156.84 (1 C, d, J=259.02 Hz), 171.77 (1 C, d, J=4.27 Hz), 171.97 (1 C, s).

7-(2-aminoethylamino)-6-fluoro-4-oxo-7-propyl-1,4-dihydroquinoline-3-carboxylic acid (I9, 60% yield). $^1$H NMR (TFAd) δ ppm: 0.89 (3 H, t, J=7.32 Hz), 1.91 (2 H, dt, J=7.14 Hz), 3.54 (2 H, s) 3.82 (2 H, s) 4.48 (2 H, t, J=6.86 Hz), 6.87 (1 H, d, J=6.22 Hz), 7.96 (1 H, d, J=10.61 Hz), 8.93 (1 H, s); NMR $^{13}$C (TFAd) δ ppm 10.64 (1 C, s) 23.18 (1 C, s) 40.87 (1 C, s) 41.37 (1C, s) 60.49 (1 C, s) 97.13 (1 C, d, J=3.85 Hz), 103.93 (1 C, s) 111.04 (1 C, d, J=23.08 Hz), 114.40 (1 C, d, J=9.40 Hz), 142.16 (1 C, s) 147.83 (1 C, d, J=14.11 Hz), 149.72 (1 C, s) 153.83 (1 C, d, J=256.03 Hz), 171.12 (1 C, d, J=4.27 Hz), 172.20 (1 C, s).

7-(diethylamino)-6-fluoro-4-oxo-1-propyl-1,4-dihydroquinoline-3-carboxylic acid (I10, 90% yield in pressurized container). $^1$H NMR (TFAd) δ ppm: 0.91 (3 H, t, J=7.41 Hz), 1.16 (6 H, t, J=7.23 Hz), 1.93 (2 H, td, J=14.59, 7.23 Hz), 3.88 (4 H, q, J=7.14 Hz), 4.68 (2 H, t, J=7.23 Hz), 8.48 (1 H, d, J=10.43 Hz), 8.53 (1 H, d, J=4.57 Hz), 9.31 (1 H, s); NMR $^{13}$C (TFAd) δ ppm 10.77 (11 C, s) 11.16 (2 C, s) 24.25 (1 C, s) 56.80 (2 C, s) 61.38 (1 C, s) 108.12 (1 C, s) 113.86 (1 C, d, J=66.25 Hz), 118.07 (1 C, d, J=6.84 Hz), 139.07 (1 C, s) 151.91 (1 C, d, J=48.73 Hz), 153.17-153.70 (1 C, m) 156.33 (1 C, d, J=259.87 Hz), 170.66 (1 C, s) 174.56 (1 C, s).

1-(3-(benzhydrylthio)propyl)-6-fluoro-7-(N-morpholinyl)-4-oxo-1,4-dihydroquinoline-3-carboxylic acid (I11, 70% yield), $^1$H NMR (DMSO-D6) δ ppm: 2.02 (2 H, dt, J=13.77, 6.93 Hz), 2.34 (2 H, t, J=6.95 Hz), 3.25 (4 H, s) 3.73 (4 H, s) 4.56 (2 H, t, J=6.31 Hz), 5.32 (1 H, s) 7.10 (1H, d, J=6.95 Hz), 7.18 (2 H, t, J=7.14 Hz), 7.25 (4 H, t, J=7.50 Hz), 7.37 (4 H, d, J=7.32 Hz), 7.90 (1 H, d, J=13.36 Hz), 20.00 (1 H, s); NMR $^{13}$C (101 MHz, DMSO-d6) δ ppm 27.20 (1 C, s) 27.47 (1 C, s) 49.13 (2 C, d, J=4.70 Hz), 51.72 (1 C, s) 51.88 (1 C, s) 65.19 (2 C, s) 105.16 (1 C, s) 106.30 (1 C, s) 110.60 (1 C, d, J=22.65 Hz), 118.78 (1 C, d, J=7.69 Hz), 126.42 (2C, s) 127.23 (4 C, s) 127.83 (4 C, s) 136.58 (1 C, s) 140.77 (1 C, s) 144.70 (1 C, d, J=9.83 Hz), 148.33 (1 C, s) 152.23 (1 C, d, J=249.62 Hz), 165.41 (1 C, s) 175.55 (1C, d, J=2.56 Hz).

1-(3-(benzhydrylthio)propyl)-6-fluoro-4-oxo-7-(N-piperazinyl)-1,4-dihydroquinoline-3-carboxylic acid. (I12, 95% yield). $^1$H NMR (TFAd) δ ppm: 2.17 (2 H, m) 2.49 (2 H, t, J=6.96 Hz), 3.35 (4 H, s) 3.72 (4 H, s) 4.75 (2 H, t, J=6.68 Hz), 5.08 (1H, s) 7.11 (2 H, t, J=7.14 Hz), 7.18 (4 H, t, J=7.32 Hz), 7.28 (4 H, d, J=7.32 Hz), 7.51 (1 H, d, J=6.22 Hz), 8.13 (1H, d, J=12.44 Hz), 9.13 (1 H, s); 13C NMR (TFAd) δ ppm: 29.31 (1 C, s) 29.58 (1C, s) 45.68 (2 C, s) 47.87 (2C, d, J=6.41 Hz), 56.90 (1 C, s) 57.22 (1 C, s) 104.92 (1 C, s) 106.66 (1 C,s) 113.60 (1 C, d, J=25.65 Hz), 117.92 (1 C, d, J=8.98 Hz), 128.22 (2C, s) 129.34 (4 C, s) 130.19 (4 C, s) 140.67 (1 C, s) 141.80 (2 C, s) 149.66 (1 C, d, J=10.69 Hz), 150.88 (1C, s) 156.48 (1 C, d, J=259.02 Hz), 171.58 (1 C, s) 172.04 (1 C, d, J=3.85 Hz).

Hapten Ic2

Solution of corresponding fluoroquinolone piperazinyl Id (0.5 mmol) and formaldehyde (2 mmol) was stirred in formic acid (1 mL) at 110° C. for 2.5 hours, and the mixture was evaporated to dryness.

Using this methodology, and corresponding fluoroquinoline piperazinyl, the following methylpiperazinyl fluoroquinolone was prepared:

6-fluoro-7-(4-methylpiperazin-1-yl)-4-oxo-1-propyl-1,4-dihydroquinoline-3-carboxylic acid. (I13, quantitative yield), $^1$H NMR (TFAd) δ ppm: 0.89 (3 H, t, J=7.32 Hz), 1.92 (1 H, td, J=14.45, 7.14 Hz), 2.97 (3 H, s) 3.31 (2 H, t, J=11.16 Hz), 3.48 (2 H, t, J=12.90 Hz), 3.69 (2 H, d, J=12.26 Hz), 3.99 (2 H, d, J=13.91 Hz), 4.55 (2 H, t, J=7.32 Hz), 7.24 (1 H, d, J=6.40 Hz), 8.09 (1 H, d, J=12.26 Hz), 9.05 (1 H, s); NMR $^{13}$C (TFAd) δ ppm: 10.71 (1 C, s) 23.57 (1 C, s) 45.28 (2 C, s) 47.94-48.53 (2 C, m, J=5.98 Hz), 55.83 (1 C, s) 60.84 (1 C, s) 105.07 (1 C, s) 107.06 (1 C, d, J=2.99 Hz), 113.66 (1 C, d, J=25.65 Hz), 118.04 (1 C, d, J=10.26 Hz), 140.81 (1 C, s) 149.51 (1 C, d, J=10.68 Hz), 150.61 (1 C, s) 156.86 (1 C, d, J=258.16 Hz), 171.77 (1 C, s) 172.28 (1 C, d, J=3.85 Hz).

B. Immunochemistry

General Procedures and Equipment

Deprotecting the thiol group of corresponding haptens was monitored by means of HPLC-UV, using a Merck-Hitachi 1-7100 pump equipped with an L-7455 diode array detector, L-7200 autosampler and D7000 interface (Merck, Darmstadt, Germany). Chromatograms were processed using HSM software (Merck, Darmstadt, Germany). A Lichrospher column 100 RP-18 125×4 (5 mm; Merck, Darmstadt, Germany) was used and analyses were carried out in gradient mode using acetonitrile (ACN): citrate buffer (50 mM, pH=3) as mobile phase to a flow of 1.0 mL min$^{-1}$. Reactions were monitored at two wavelengths: 330 nm and 280 nm. The MALDI-TOF-MS (Matrix-Assisted Laser Desorption/Ionization with Time-Of-Flight) used to analyze protein conjugates was a Perspective BioSpectrometry Workstation equipped with Voyager-DE-RP software (version 4.03) developed by Perspective Biosystems Inc. (Framingham, Mass.) and Grams/386 (for Microsoft Windows, version 3.04, level III) developed by Galactic Industries Corporation (Salem, N.H.).

Analysis of Hapten Density

Hapten densities of protein conjugates were estimated by means of MALDI-TOF-MS comparing molecular weight of natural proteins with that of conjugates. MALDI experiments were conducted by mixing 2 µL of freshly prepared matrix (trans-3,5-dimethoxy-4-hydroxycinnamic acid, 10 mg mL$^{-1}$ in ACN/H$_2$O 70:30, TFA at 0.1%) with 2 µL of conjugates or proteins conjugates in ACN/H$_2$O 70:30, TFA at 0.1% (5 mg mL$^{-1}$). Hapten density was estimated ($δ_{Hapten}$) according to the following equation:

$$[PM(\text{Conjugate}) - PM(\text{Protein})] / PM(\text{Hapten}).$$

The pH and conductivity of all the buffers and solutions were measured with a pH meter pH 540 GLP and LF 340 conductivity meter, respectively (WTW, Weilheim, Germany). Polystyrene microtiter plates were purchased from Nunc (Maxisorp, Roskilde, DK). ELISA wash stops were carried out by PW SLY96 microplate washer (SLT Labinstruments GmbH, Salzburg, Austria). Absorbances were read on a SpectramaxPlus (Molecular Devices, Sunnyvale, Calif.). Competition curves were analyzed with a four parameter logistic equation using SoftmaxPro v2.6 software (Molecular Devices) and GraphPad Prism (GraphPad Software Inc., San Diego, Calif.).

Chemical and Immunochemical Products

Immunochemical products were obtained from Sigma Chemical Co. (San. Luis, Mo.). Chemical products used for cross-reactivity studies were purchased from Aldrich Chemical Co. (Milwaukee, Wis.).

Buffers

Phosphate buffered saline (PBS) solution is a 0.01M phosphate buffer solution in 0.8% saline, and the pH is 7.5. PBST is PBS with 0.05% Tween 20. Borate buffer is boric acid/borate sodium 0.2M pH=8.7. Coating buffer is a 0.05M carbonate-bicarbonate buffer, pH 9.6. Citrate buffer is a 0.04M sodium citrate solution, pH 5.5. Substrate solution contains 0.01% TMB (3,3',5,5'-tetramethylbenzidine) and 0.004% $H_2O_2$ in citrate buffer.

Preparation of Immunoreactive Agents

Ie and If Immunoreactive Agents

Haptenization of immunogenic carriers in the case of haptens that have a thiol group was carried out by a three-stage sequence, which is described below.

Stage 1: Activation of Proteins (VII). A solution of corresponding succinimidyl ester VI (70 μmol) in anhydrous DMF (400 μL) was added dropwise to a protein solution (15 mg) in borate buffer, and pH was adjusted to 8 using triethylamine. Mixture was kept at 4° C. overnight, and protein activated by exclusion chromatography was purified using a Sephadex G-25 Superfine HiTrap desalting column of 5 mL (Amersham Biosciences) and borate buffer as eluent. Eluted fractions of activated proteins were collected (0.5 mL), and those with positive result were combined in the assay of Bradford protein (3 mL) (Bradford, M. M. *Analytical Biochemistry* 1976, 72, 248-254). Part of this solution was reserved for MALDI-TOF-MS analysis and the remainder was used for conjugation as described in Stage 3.

Thus, using corresponding succinimidyl ester, the following proteins were activated:

3-maleimidopropanoato BSA (VIIa). $\delta_{Hapten}$ (mol Hapten/mol protein): 31.29. Iodoacetate BSA (VIIb). $\delta_{Hapten}$ (mol Hapten/mol protein): 15.62.

Stage 2. Deprotection (Id). Hapten was dissolved with protected thiol group Ia, b, c (0.18 mmol) and anisole (2.74 mmol) in trifluoroacetic acid (2 mL), and the resulting mixture was stirred at 45° C. for 1.5 h until total conversion of starting material was observed through HPLC-UV. At this time, the solvent was evaporated to dryness under vacuum and the residue was dissolved in water and washed with dichloromethane. Aqueous layer was used immediately for conjugation without further purification, as described in Stage 3.

Thus, corresponding haptens with free thiol group were obtained:

6-fluoro-1-(3.mercaptotropyl)-7-(N-morpholinyl)-4-oxo-1,4-dihydroquinoline-3-carboxylic acid (I14, 68% yield), $^1$H NMR (CDCl$_3$) δ ppm: 1.60 (1 H, t, J=8.06 Hz), 2.21 (2 H, tt, J=7.08, 6.84 Hz), 2.69 (2 H, q, J=7.57, 6.84, 5.86 Hz), 3.32 (4 H, t, J=4.64 Hz), 3.91 (4 H, t, J=4.64 Hz), 4.44 (2 H, t, J=7.57 Hz), 7.01 (1 H, d, J=6.84 Hz), 8.07 (1 H, d, J=13.18 Hz), 8.69 (1 H, s); NMR $^{13}$C (CDCl$_3$) δ ppm: 21.43 (1 C, s) 32.39 (1 C, s) 50.51 (2 C, s) 52.80 (1 C, s) 66.80 (2 C, s) 104.05 (1 C, s) 108.70 (1 C, s) 113.28 (1 C, d, J=26.55 Hz), 121.01 (1 C, s) 137.52 (1 C, s) 146.34 (1 C, d, J=10.98 Hz), 148.03 (1 C, s) 153.77 (1 C, d, J=253.12 Hz), 167.42 (1 C, d, J=0.91 Hz), 177.28 (1 C, d, J=2.29 Hz).

6-fluoro-1-(3-mercaptotropyl)-4-oxo-7-(N-piperazinyl)-1,4-dihydroquinoline-3-carboxylic acid (I15, 45% yield), $^1$H NMR (D$_2$O) δ ppm: 1H 2.54 (2 H, s) 2.87-3.00 (2 H, m) 3.78-4.06 (4 H, m) 4.07-4.22 (4 H, m) 4.92-5.33 (2 H, m) 7.86 (1 H, d, J=6.35 Hz), 8.46 (1 H, d, J=12.21 Hz), 9.51 (1 H, s); $^{13}$C NMR (D$_2$O) δ ppm: 21.49 (1 C, s), 32.87 (1 C, s), 44.17 (2 C, s), 47.44 (2 C, d, J=5.17 Hz), 54.18 (1C, s), 106.69 (1 C, s), 106.82 (1 C, s), 111.85 (1 C, d, J=23.92 Hz), 120.02 (1 C, d, J=8.41 Hz), 138.05 (1 C, s), 145.78 (1 C, d, J=10.34 Hz), 149.32 (1C, s), 153.99 (1 C, d, J=251.52 Hz), 169.54 (1 C, s), 176.35 (1 C, d, J=1.94 Hz).

Stage 3 Bioconjugation (Ie, If). Aqueous phase of hapten with unprotected thiol group Id of Stage 2 was added dropwise on the activated protein solution VII purified in Stage 1. pH was adjusted to 8 using triethylamine. The mixture was kept under gentle stirring for 2.5 hours at room temperature. Finally, immunoreactive agents were purified by dialysis against PBS 0.5 mM (4×5 L) and milliQ water (1×5 L) and then lyophilized.

Using this methodology, the following immunoreactive agents were prepared:

1-[3-(2-acetamide BSA)tiopropyl]-6-fluoro-7-(N-morpholinyl)-4-oxo-1,4-dihydroquinoline-3-carboxylic acid. (I16). $\delta_{Hapten}$ (mol Hapten/mol protein): 2.23.

1-[3-(2,5-dioxo-1-(3-(BSA carboxamide)propyl)pyrrolidin-3-ylthio)propyl]-6-fluoro-4-oxo-7-(N-piperazinyl)-1,4-dihydroquinoline-3-carboxylic acid. (I17). $\delta_{Hapten}$ (mol Hapten/mol protein): 12.46.

1-[3-(2-acetamide HCH)tiopropyl]-6-fluoro-7-(N-piperacinyl)-4-oxo-1,4-dihydroquinoline-3-carboxylic acid. (I18). $\delta_{Hapten}$(mol Hapten/mol protein) (quantitative UV): 14.37

1-[3-(2-acetamide BSA)tiopropyl]-6-fluoro-7-(N-piperazinyl)-4-oxo-1,4-dihydroquinoline-3-carboxylic acid. (I19). $\delta_{Hapten}$ (mol Hapten/mol protein): 14.15.

Ig and Ih Immunoreactive Agents

Haptenization of immunogenic carriers in the case of haptens that have an acid or amine group was carried out as follows.

A solution of hapten Ib, c (10 μmol) in DMF (100 μL) was added to a protein solution (10 mg) in milliQ water (1 mL) followed by the addition of EDC solution (50 μmol) in milliQ water (100 μmol), and then the mixture was stirred for 3 hours at room temperature. Protein conjugates were purified by dialysis against PBS 0.5 mM (4×5 L) and milliQ water (1×5 L) and then lyophilized.

Using this methodology, the following immunoreactive agents were prepared:

6,7-difluoro-4-oxo-1,4-dihydroquinoline-3-carboxamide BSA. (I20). MS $\delta_{Hapten}$ (mol Hapten/mol protein): 7.11.

6,7-difluoro-4-oxo-1,4-dihydroquinoline-3-carboxamide CONA (I21). $\delta_{Hapten}$ (mol Hapten/mol protein): 2.60.

6,7-difluoro-1-propyl-4-oxo-1,4-dihydroquinoline-3-carboxamide BSA (I22). $\delta_{Hapten}$ (mol Hapten/mol protein): 3.74.

6,7-difluoro-1-propyl-4-oxo-1,4-dihydroquinoline-3-carboxamide CONA (I23). $\delta_{Hapten}$ (mol Hapten/mol protein): 1.09.

6-fluoro-7-(N-morpholinyl)-4-oxo-1,4-dihydroquinoline-3-carboxamide BSA (I24). $\delta_{Hapten}$ (mol Hapten/mol protein): 1.37.

6-fluoro-7-(N-morpholinyl)-4-oxo-1-propyl-1,4-dihydroquinoline-3-carboxamide BSA (I25). $\delta_{Hapten}$ (mol Hapten/mol protein): 1.79.

7-[2-(BSA acetamide)ethylamino]-6-fluoro-4-oxo-1-propyl-1,4-dihydroquinoline-3-carboxylic acid. (I26). $\delta_{Hapten}$ (mol Hapten/mol protein): 5.28.

7-(diethylamino)-6-fluoro-4-oxo-1-propyl-1,4-dihydroquinoline-3-carboxamide BSA (I27). $\delta_{Hapten}$ (mol Hapten/mol protein): 4.62.

7-(diethylamino)-6-fluoro-4-oxo-1-propyl-1,4-dihydro-quinoline-3-carboxamide CONA (I28). $\delta_{Hapten}$ (mol Hapten/mol protein): 4.30.

6-fluoro-7-(4-methylpiperazin-1-yl)-4-oxo-1-propyl-1,4-dihydroquinoline-3-carboxamide BSA (I29). $\delta_{Hapten}$ (mol Hapten/mol protein): 2.16.

6-fluoro-7-(4-methylpiperazin-1-yl)-4-oxo-1-propyl-1,4-dihydroquinoline-3-carboxamide CONA (I30). $\delta_{Hapten}$ (mol Hapten/mol protein): 1.36.

Ii Immunoreactive Agent

Haptenization of immunogenic carriers in the case of haptens that have an amino group was carried out by a two-stage sequence, which is described below.

A cyanuric chlorine solution (1.5 μmol) was added in DMF (150 μL) to a protein solution (6 mg) in carbonate buffer with pH 9.6 (1 mL). The mixture was kept under room temperature for 2 hours, and then a solution of corresponding hapten Ic (2 μmol) was added dropwise in DMF (60 μL). The mixture was kept under gentle stirring for 4 hours at 37° C. Finally, immunoreactive agents were purified by dialysis against PBS 0.5 mM (4×5 L) and milliQ water (1×5 L) and then lyophilized.

Using this methodology, the following immunoreactive agents were prepared:

7-[2-(4-chloro-6-HRP-1,3,5,-triazine-2-ylamino)ethyl-amino]-6-fluoro-4-oxo-1-propyl-1,4-dihydroquinoline-3-carboxylic acid. (I31). $\delta_{Hapten}$ (mol Hapten/mol protein): 1.76.

Preparation of Polyclonal Antiserum

Immunization protocol was conducted in female white rabbits from New Zealand weighing 1-2 Kg, as described previously (Salvador, *Analytical Chemistry*. 2007, 79, 3734-3740). Immunogens (100 μg) dissolved in PBS (0.5 mL) were emulsified with Freund's adjuvant, completely the first time and the remainder incompletely, in 1:1 ratio. They were rapidly injected intradermally in different places of the host animal back (one injection per month). Antibody titers evolution was assessed by measuring serial dilutions binding of different antiserum in microtiter plates coated with the corresponding immunoreactive agent. After observing an acceptable antibody titer, animals were bled to death and their blood was collected in Vacutainer tubes fitted with a serum separating gel. Antiserum were obtained by centrifugation and stored at −80° C. in the presence of 0.02% $NaN_3$.

Development of Competitive Indirect ELISAs for Quinolones

Microtiter plates were coated with corresponding coating antigen (indirect format) or antiserum (direct format) dissolved in coating buffer (100 μL/well) overnight at 4° C. or during 4 hours at room temperature and covered with airtight adhesive plates. Subsequently, plates were washed with PBST (four times, 300 μL/well) and quinolone patters were added (0.01 nM-10000 nM, in PBST, 50 μL/well) followed by the corresponding antiserum (indirect format) or enzymatic tracer (direct format) (50 μL/well) in microtiter plates. After 30 minutes at room temperature, plates were washed as described above and, in the case of indirect format, a solution of antiIgG rabbit IgG labelled with HRP (1/6000 in PBST) (100 μl/well) was added and incubated for 30 minutes at room temperature. Plates were washed again, and for both formats, substrate solution was added (100 μL/well). Color development was stopped after 30 minutes at room temperature with $4H_2SO_4N$ (50 μL/well), and absorbance was read at 450 nm. Standard curves were adjusted to a four parameter equation, using the following formula: $Y=[(A-B)/1-[x/C)D]+B$, where A represents maximum absorbance, B represents minimum absorbance, C represents the concentration producing 50% of maximum absorbance, and D represents the tangent at the inflection point of sigmoid curve.

Thus, the following competitive ELISAs were obtained for ciprofloxacin:

TABLE 1

Parameters of competitive ELISA assays for detection of ciprofloxacin using immunoreactive agents and antibodies developed with immunoreactive agents described in this invention.

| As | IR | [IR] μg/mL | [As] Dilution | Max. Abs. | Min. Abs. | IC50 μg/L | Slope | $R^2$ |
|---|---|---|---|---|---|---|---|---|
| 171 | I16 | 2.5 | 1/16000 | 1.767 | 0.137 | 16.40 | −0.857 | 0.9980 |
| 171 | I19 | 0.0156 | 1/128000 | 1.615 | 0.073 | 4.81 | −0.661 | 0.9985 |
| 171 | I26 | 0.25 | 1/16000 | 1.360 | 0.098 | 1.66 | −0.793 | 0.9691 |
| 172 | I16 | 2.5 | 1/4000 | 1.900 | 0.090 | 38.39 | −0.770 | 0.9959 |
| 172 | I19 | 0.0156 | 1/32000 | 1.817 | 0.088 | 27.60 | −0.646 | 0.9928 |
| 172 | I26 | 0.25 | 1/4000 | 1.427 | 0.079 | 11.56 | −0.845 | 0.9939 |
| 173 | I16 | 5 | 1/16000 | 1.748 | 0.144 | 134.68 | −0.538 | 0.9959 |
| 173 | I19 | 0.0156 | 1/128000 | 1.710 | 0.165 | 48.55 | −0.547 | 0.9939 |
| 173 | I26 | 0.25 | 1/16000 | 0.915 | 0.013 | 1.49 | −0.253 | 0.9825 |
| 171 | I31 | 0.0625 | 1/8000 | 1.49 | 0.032 | 0.81 | −1.46 | 0.9952 |

Determination of Cross-Reactivity

Stock solutions were prepared at a concentration of 10 nM for different quinolones and other antibiotics in sodium hydroxide (50 nM) and measured by ELISA. Cross-reactivity values were calculated according to the equation below: ($DI_{50}$ CPFX/$DI_{50}$ of tested compounds)×100.

The following table shows $IC_{50}$ and cross-reactivity values using immunoreactive agents and antibodies developed in this invention.

TABLE 2

$IC_{50}$ and cross-reactivity data for various antibiotics using antibodies developed with immunoreactive agents described herein.

| Compound | $IC_{50}$ (μg·$L^{-1}$) | % CR |
|---|---|---|
| Ciprofloxacin | 0.77 ± 0.27 | 100 |
| Enrofloxacin | 0.65 | 95 |
| Danofloxacin | 7.31 | 8 |
| Difloxacin | 0.91 | 75 |
| Marbofloxacin | 4.30 | 28 |
| Flumequine | 3.91 | 22 |
| Oxolinic acid | 23.53 | 4 |
| Norfloxacin | 0.78 | 81 |
| Sarafloxacin | 0.96 | 80 |
| Ofloxacin | 1.84 | 39 |

TABLE 2-continued

IC$_{50}$ and cross-reactivity data for various antibiotics using antibodies developed with immunoreactive agents described herein.

| Compound | IC$_{50}$ (µg·L$^{-1}$) | % CR |
|---|---|---|
| Sulfamethazine | >1000 | <0.2 |
| Sulfathiazole | >1000 | <0.2 |
| Chloramphenicol | >1000 | <0.2 |
| Tetracycline | >1000 | <0.2 |
| Doxycycline | >1000 | <0.2 |
| Ampicillin | >1000 | <0.2 |

The invention claimed is:

1. A method for obtaining a polyclonal antibody against quinolone antibiotics comprising the following steps:
  a) mixing an immunogenic carrier with a bifunctional linking compound in order to get an activated immunogenic carrier;
  b) reacting the activated immunogenic carrier with a quinolone compound in order to get a conjugate, wherein said conjugate is 1-[3-(2-acetamide HCH) thiopropyl]-6-fluoro-7-(N-piperazinyl)-4-oxo-1,4-dihydroquinoline-3-carboxylic acid, wherein HCH is horseshoe crab hemocyanin;
  c) eliciting an in vivo humoral response against said conjugate obtained in (b) to generate the polyclonal antibody; and
  d) isolating the polyclonal antibody generated in (c).

2. A method for detection and/or quantification of quinolone antibiotics, comprising the following steps:
  obtaining a polyclonal antibody against the quinolone antibiotics according to the method of claim 1;
  performing a competitive immunoassay, comprising:
    (a) contacting said polyclonal antibody, a secondary immunoreagent, and a sample potentially containing the quinolone antibiotics, wherein the secondary immunoreagent is 7-[2-(BSA acetamide)ethylamino]-6-fluoro-4-oxo-1-propyl-1,4-dihydroquinoline-3-carboxylic acid or 7-[2(4-chloro-6-HRP-1,3,5,-triazine-2-ylamino)ethylamino]-6-fluoro-4-oxo-1-propyl-1,4-dihydroquinoline-3-carboxylic acid, wherein BSA is bovine serum albumin and HRP is horseradish peroxidase;
    (b) executing a competition reaction between the secondary immunoreagent and the quinolone antibiotics in the sample for the polyclonal antibody;
    (c) introducing components and/or reagents necessary to generate a measurable signal;
  performing an analysis on the measurable signal for detecting and/or quantifying the presence of the quinolone antibiotics according to the results of the competition reaction.

3. The method according to claim 2, wherein the sample is a product of animal origin intended for food consumption.

4. The method of claim 3 wherein the product of animal origin is milk.

* * * * *